(12) United States Patent
Biedermann et al.

(10) Patent No.: US 9,867,639 B2
(45) Date of Patent: Jan. 16, 2018

(54) SCREW ELEMENT FOR USE IN SPINAL, ORTHOPEDIC OR TRAUMA SURGERY AND A SYSTEM OF SUCH A SCREW ELEMENT AND A SCREW DRIVER ADAPTED THERETO

(71) Applicant: BIEDERMANN TECHNOLOGIES GMBH & CO. KG, Donaueschingen (DE)

(72) Inventors: Lutz Biedermann, VS-Villingen (DE); Dimosthenis Dandanopoulos, VS-Schwenningen (DE); Wilfried Matthis, Weisweil (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 14/685,433

(22) Filed: Apr. 13, 2015

(65) Prior Publication Data

US 2015/0289905 A1 Oct. 15, 2015

Related U.S. Application Data

(60) Provisional application No. 61/979,818, filed on Apr. 15, 2014.

(30) Foreign Application Priority Data

Apr. 15, 2014 (EP) .................................. 14164692

(51) Int. Cl.
*A61B 17/70* (2006.01)
*A61B 17/86* (2006.01)
*A61B 17/88* (2006.01)

(52) U.S. Cl.
CPC ...... *A61B 17/7002* (2013.01); *A61B 17/7059* (2013.01); *A61B 17/7082* (2013.01);
(Continued)

(58) Field of Classification Search
CPC ............ A61B 17/7082; A61B 17/8875; A61B 17/7071; A61B 17/7091
(Continued)

(56) References Cited

U.S. PATENT DOCUMENTS 2,140,449 A * 12/1938 Brown .......................... 411/410
2,538,350 A * 1/1951 Baule ............................ 411/403
(Continued)

FOREIGN PATENT DOCUMENTS

WO WO 2014/035764 A1 3/2014

OTHER PUBLICATIONS

European Search Report and Opinion issued by the EPO for EP 14164692.7 dated Sep. 11, 2014 (6 pages).

*Primary Examiner* — Eduardo C Robert
*Assistant Examiner* — Michelle C Eckman
(74) *Attorney, Agent, or Firm* — Lewis Roca Rothgerber Christie LLP

(57) ABSTRACT

A screw element includes a screw axis, a shank for inserting in a bone, and a drive portion for engaging a screw driver. The drive portion includes a first wall defining a first recess and a second wall defining a second recess. Drive grooves are formed in the first wall and extend parallel to the screw axis. The second wall extends axially from a free end portion of the screw element to the first wall and has an inner diameter that continuously increases from the first wall towards the free end portion. A plurality of guide grooves are formed in the second wall at circumferential positions corresponding respectively to circumferential positions of the drive grooves. The guide grooves extend further radially (Continued)

from the screw axis than the drive grooves and guide the screw driver from the free end portion of the screw element to the drive grooves.

23 Claims, 6 Drawing Sheets

(52) U.S. Cl.
CPC ........ *A61B 17/8615* (2013.01); *A61B 17/888* (2013.01); *A61B 17/8888* (2013.01)

(58) Field of Classification Search
USPC .......................... 606/308, 104; 411/402–410
See application file for complete search history.

(56) References Cited

U.S. PATENT DOCUMENTS

| | | | | |
|---|---|---|---|---|
| 5,019,080 | A * | 5/1991 | Hemer | 606/104 |
| 5,105,690 | A * | 4/1992 | Lazzara et al. | 81/436 |
| 5,435,680 | A * | 7/1995 | Schuster | 411/404 |
| 5,553,983 | A * | 9/1996 | Shinjo | 411/404 |
| 5,697,979 | A * | 12/1997 | Pignataro | 623/15.11 |
| 6,048,343 | A * | 4/2000 | Mathis et al. | 606/916 |
| 6,302,632 | B1 * | 10/2001 | Lin | 411/404 |
| 6,685,412 | B2 * | 2/2004 | Altarac et al. | 411/403 |
| 6,746,186 | B2 * | 6/2004 | Ukai | 408/226 |
| 6,948,408 | B1 * | 9/2005 | Lee | 81/436 |
| 6,988,432 | B2 * | 1/2006 | Brooks | 81/439 |
| 7,730,812 | B2 * | 6/2010 | Edland | 81/460 |
| 8,291,795 | B2 * | 10/2012 | Hughes et al. | 81/460 |
| 2003/0113690 | A1 * | 6/2003 | Hollander et al. | 433/173 |
| 2004/0062623 | A1 * | 4/2004 | Hughes | 411/403 |
| 2006/0293677 | A1 * | 12/2006 | Oepen | 606/73 |
| 2007/0043379 | A1 * | 2/2007 | Sullivan et al. | 606/104 |
| 2007/0274800 | A1 * | 11/2007 | Mikkonen et al. | 411/15 |
| 2008/0249570 | A1 * | 10/2008 | Carson et al. | 606/264 |
| 2008/0269768 | A1 * | 10/2008 | Schwager et al. | 606/104 |
| 2009/0105716 | A1 * | 4/2009 | Barrus | 606/103 |
| 2009/0105769 | A1 * | 4/2009 | Rock et al. | 606/308 |
| 2010/0125302 | A1 * | 5/2010 | Hammill et al. | 606/308 |
| 2010/0198272 | A1 * | 8/2010 | Keyer et al. | 606/302 |
| 2010/0256688 | A1 * | 10/2010 | Giersch et al. | 606/305 |
| 2010/0262196 | A1 * | 10/2010 | Barrus et al. | 606/308 |
| 2011/0077693 | A1 * | 3/2011 | Yu | 606/305 |
| 2011/0093021 | A1 * | 4/2011 | Fanger et al. | 606/308 |
| 2011/0106166 | A1 * | 5/2011 | Keyer | A61B 17/705 606/264 |
| 2011/0172719 | A1 * | 7/2011 | Gorhan et al. | 606/305 |
| 2011/0245839 | A1 * | 10/2011 | Lower | 606/104 |
| 2011/0306984 | A1 * | 12/2011 | Sasing | 606/104 |
| 2012/0078307 | A1 * | 3/2012 | Nihalani | 606/264 |
| 2012/0137842 | A1 * | 6/2012 | Guo et al. | 81/460 |
| 2012/0165107 | A1 * | 6/2012 | Guo et al. | 470/57 |
| 2013/0030476 | A1 * | 1/2013 | Shimko et al. | 606/308 |
| 2013/0190825 | A1 * | 7/2013 | Perrow et al. | 606/281 |
| 2013/0197585 | A1 * | 8/2013 | Jackson et al. | 606/278 |
| 2013/0211465 | A1 * | 8/2013 | Savage | 606/308 |
| 2014/0005728 | A1 * | 1/2014 | Koay et al. | 606/281 |
| 2014/0005731 | A1 * | 1/2014 | Biedermann et al. | 606/328 |
| 2014/0066945 | A1 * | 3/2014 | Humphreys | A61B 17/8615 606/104 |
| 2014/0142632 | A1 * | 5/2014 | Keyer et al. | 606/265 |
| 2014/0214084 | A1 * | 7/2014 | Jackson et al. | 606/270 |
| 2014/0236247 | A1 * | 8/2014 | Rezach | 606/308 |
| 2014/0257408 | A1 * | 9/2014 | Trieu et al. | 606/301 |
| 2015/0089787 | A1 * | 4/2015 | Schon et al. | 29/426.5 |
| 2015/0112355 | A1 * | 4/2015 | Dahners et al. | 606/104 |

* cited by examiner

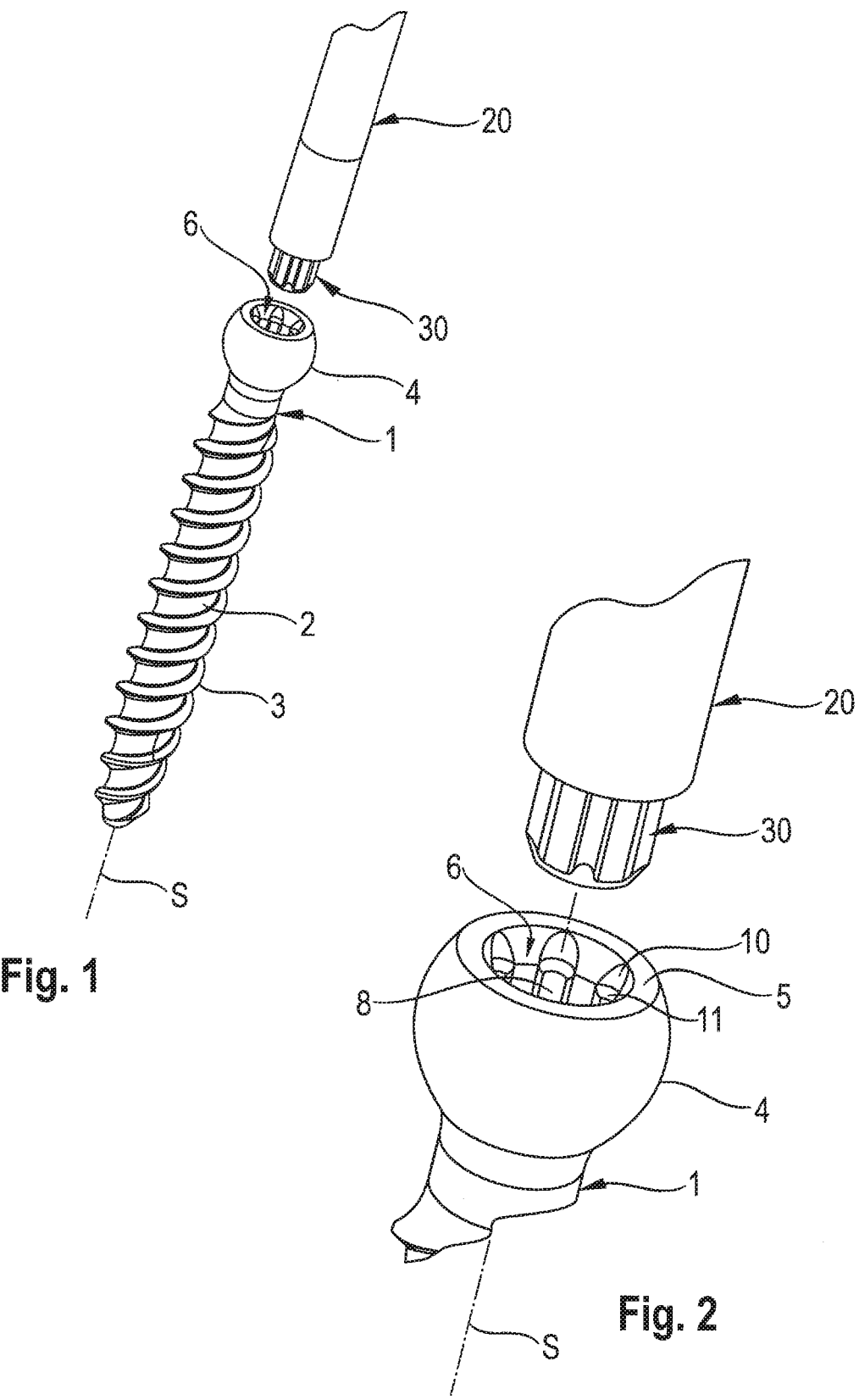

SCREW ELEMENT FOR USE IN SPINAL, ORTHOPEDIC OR TRAUMA SURGERY AND A SYSTEM OF SUCH A SCREW ELEMENT AND A SCREW DRIVER ADAPTED THERETO

CROSS-REFERENCE TO RELATED APPLICATIONS

The present disclosure claims benefit of the U.S. Provisional Patent Application Ser. No. 61/979,818, filed on Apr. 15, 2014, the contents of which are hereby incorporated by reference in their entirety, and claims priority from European Patent Application EP 14164692.7, filed on Apr. 15, 2014, the contents of which are hereby incorporated by reference if their entirety.

BACKGROUND

Field of the Invention

The invention relates to a screw element for use in spinal, orthopedic or trauma surgery, and to a screw driver adapted for use with the screw element. The screw element includes a drive portion for engagement with a screw driver, wherein the drive portion includes drive grooves for engagement with corresponding engagement protrusions of the screw driver, and guide grooves that are configured to guide the engagement protrusions of the screw driver into the drive grooves. The screw element can be used in particular in minimally invasive surgery and other procedures, such as minimal access surgery, where the visibility of and/or access to the operation site is reduced.

Description of the Related Art

In spinal surgery, surgical techniques are known that include a step of mounting a receiving part of a polyaxial pedicle screw onto the screw element in situ after placement of the screw element into the pedicle of a vertebra. For example, in a surgical technique known as interpedicular minimal access surgery, a small incision is made and several motion segments of the spine are treated through the small incision. First, the screw elements with ball-shaped heads are inserted into the pedicles using an instrument that holds the screw elements so that they do not accidentally detach from the instrument, and where the instrument also acts as a screw driver to insert the screw elements. The screw elements are inserted into the pedicles to a certain depth that might not be the final insertion depth for the screw elements. Then, the actual insertion depths are determined with the aid of, for example, an X-ray image, and thereafter the screw elements are more precisely adjusted to a final desired insertion depth on the basis of the X-ray image. Finally, the receiving parts are mounted onto the screw elements and a stabilization rod is connected to the receiving parts.

During the step of adjusting the insertion depth of the respective screw elements, a screw driver that is configured to engage a drive portion of the screw element is used. With known screw elements and drivers, locating the drive portion of the screw element may be difficult if visibility of the operation site is restricted or if the respective screw element is not visible at all.

SUMMARY

Embodiments of the present invention provide a screw element and a system of a screw element and a corresponding screw driver adapted thereto that allows for adjustment of an insertion depth of the screw element in a quick and safe manner.

The screw element permits the screw driver to more easily locate the corresponding drive portion on the screw element. In addition, the screw element facilitates insertion of the engagement portion of the screw driver into the drive portion of the screw element. Therefore, even when the screw driver is inserted at a slight incline relative to the screw element, the design of the drive portion of the screw element helps align the screw axis and the axis of the screw driver. Further, operation of the screw driver does not require any complex functions, which allows for easy and convenient handling.

The screw element may be a bone screw with a head that includes the drive portion. However, the screw element may also be a set screw that is used as a locking element in a receiving part of a polyaxial bone screw or in a bone plate. More generally, the screw element may be used to adjust the position of a screw that has already been placed or implanted when there is limited or no visibility at the operation site.

BRIEF DESCRIPTION OF THE DRAWINGS

Further features and advantages of the invention will become apparent from the description of embodiments by means of the accompanying drawings. In the drawings:

FIG. 1 shows a perspective view of a screw element and a portion of a screw driver adapted to a drive portion of the screw element according to a first embodiment of the present invention.

FIG. 2 shows an enlarged view of a detail of FIG. 1.

DETAILED DESCRIPTION

Figure 3:
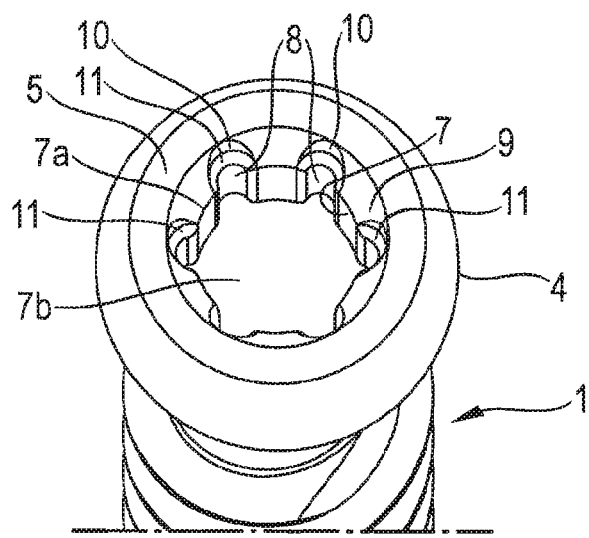
FIG. 3 shows a perspective view from a top of the screw element of FIGS. 1 and 2.

Referring to FIGS. 1 to 5, a screw element 1 according to a first embodiment includes a shank 2 with a bone thread (or a screw thread) 3 on at least a portion of the shank 2 and a head 4. The shank 2 is configured to be inserted into a bone, for example, into a pedicle of a vertebra. A screw axis S is defined by the axis of the bone thread 3. The head 4 has a spherical segment shape and a free end 5 on a side that is opposite to the shank 2. A drive portion 6 that is configured to engage with an engagement portion of a screw driver is provided at the free end 5. The drive portion 6 is explained in more detail below.

A system according to an embodiment of the invention includes the screw element 1 with the drive portion 6 and a screw driver 20 that has an engagement portion 30 adapted for engagement with the drive portion 6 of the screw element 1.

Figure 4:
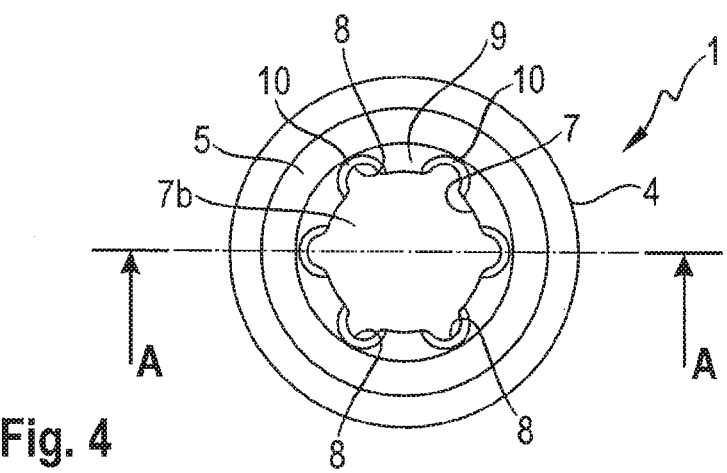
FIG. 4 shows a top view of the screw element of FIGS. 1-3.
Figure 5:
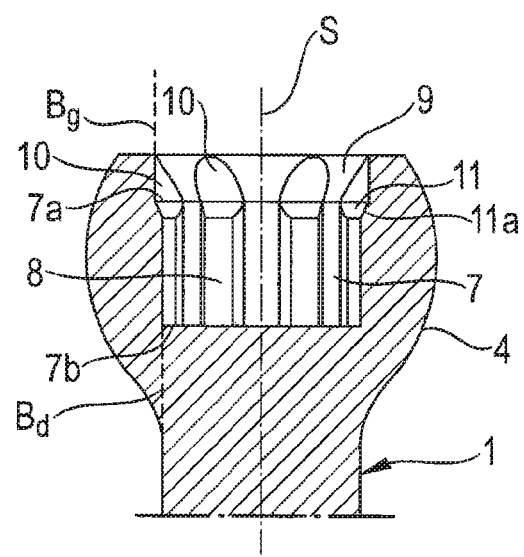
FIG. 5 shows a cross-sectional view of the screw element of FIGS. 1-4 along line A-A in FIG. 4.

As depicted in FIGS. 3 to 5, the drive portion 6 of the screw element 1 defines a first recess 7 that is located at a distance from the free end 5 and that has an inner wall with a substantially cylindrical main contour with a main inner diameter and with a cylinder axis coaxial with the screw axis S. A plurality of longitudinal drive grooves 8 are formed on the inner wall of the substantially cylindrical first recess 7. The drive grooves 8 each has a bottom defining or extending along a longitudinal bottom line $B_d$ that is parallel to the screw axis S (see FIG. 5). A cross-section of each of the drive grooves 8, taken along a plane perpendicular to the screw axis S, is substantially circular segment-shaped. From a top view, the drive grooves 8 are arranged circumferentially around the first recess 7 in a star-like manner, as shown in FIG. 4. In one embodiment, the first recess 7 and the drive grooves 8 together form a torx-shaped drive structure that is configured to be engaged by a torx-shaped engagement portion of the screw driver. An upper end 7a of the recess 7 is positioned at a distance from the free end 5 of the head 4. An axial depth from the upper end 7a to a lower end 7b of the first recess 7 substantially corresponds to a depth of usual drive recesses for screw elements of this type. In other words, the size of the first recess 7 with the drive grooves 8 is sufficient for applying a necessary torque for inserting or advancing the screw element 1.

Between the first recess 7 and the free end 5 is a second recess 9 that conically tapers and narrows from the free end 5 towards the first recess 7. A lower diameter of the second recess 9 may be slightly larger than the main diameter of the first recess 7 and an upper diameter of the second recess 9 is greater than the lower diameter of the second recess 9. The depth of the second recess 9 in the axial direction corresponds to approximately one fifth to one third of the depth of the first recess 7, preferably between one fourth and one third of the depth of the first recess 7. The second recess 9 provides an enlarged bevelled surface that facilitates insertion of the engagement portion 30 of the screw driver 20 into the drive portion 6.

A plurality of guide grooves 10 are provided in the wall defining the second recess 9 at positions corresponding to the positions of the drive grooves 8 in the first recess 7. Each of the guide grooves 10 has a bottom defining or extending along a longitudinal bottom line $B_g$ that is parallel to the screw axis S and also parallel to the bottom line $B_d$ of the corresponding drive groove 8. The bottom lines $B_g$ of the guide grooves 10 are farther away from the screw axis S than the bottom lines $B_d$ of the drive grooves 8 are from the screw axis S in a radial direction. Hence, the guide groove 10 is arranged at an axial position that is closer to the free end 5 and also extends farther from the screw axis S in the radial direction than the corresponding drive groove 8. Due to the bevelled surface of the second recess 9, the depth of the guide grooves 10 gradually increases from the free end 5 towards the guide groove 8 relative to the second recess 9. This allows for more precise guiding of an engagement protrusion 31 of the screw driver 20 into the first recess 7 while simultaneously facilitating the engagement of the engagement protrusion 31 with the outermost portion of the guide groove 10 at or near the free end 5.

As can be seen from the top view of FIG. 4, each of the guide grooves 10 has a greater width than each of the drive grooves 8. A transverse width of each of the guide grooves 10 decreases along a radial direction from the screw axis S towards the bottom line $B_g$, and due to the tapering of the second recess 9, a maximum width of each of the guide grooves 10 also decreases in a direction towards the free end 5.

The guide grooves 10 connect to (or are in communication with) the drive grooves 8 through an intermediate section (or an inclined shoulder) 11 with a bevelled wall 11a that conically narrows towards the drive grooves 8. The intermediate section 11 may have a considerably smaller axial height than the axial heights of the first recess 7 and the second recess 9. Accordingly, the intermediate section 11 and the guide grooves 10 form pocket-like recesses that catch and guide the engagement protrusions 31 of the screw driver 20 into the guide grooves 8.

Figure 6:
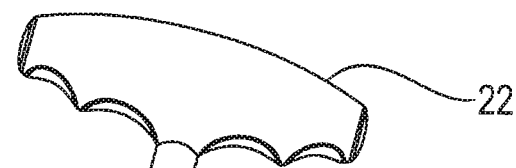
FIG. 6 shows a side view of a screw driver with an engagement portion adapted to the drive portion of the screw element of FIGS. 1-5.
Figure 7:
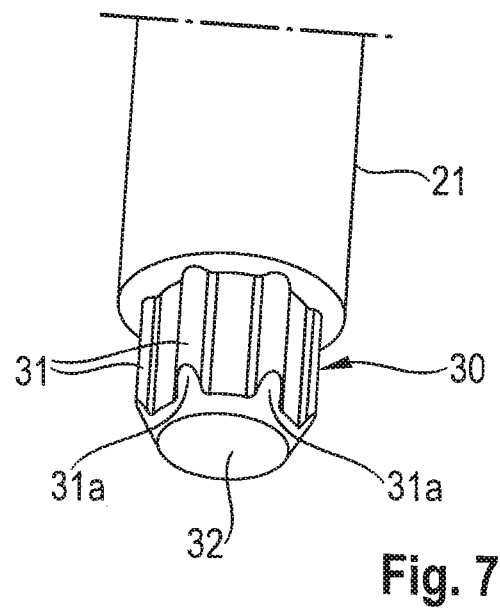
FIG. 7 shows an enlarged perspective view of the engagement portion of the screw driver of FIG. 6.

As depicted in FIGS. 6 and 7, the screw driver 20 includes a drive shaft 21, a handle 22 at one end of the drive shaft 21 and the engagement portion 30 at the opposite end of the drive shaft 21. The engagement portion 30 has a substantially cylindrical main contour that fits into the first recess 7, and longitudinally extending rib-like engagement protrusions 31 that are sized to engage the drive grooves 8 to apply torque onto the screw element 1. The engagement portion 30 is bevelled towards a free end surface 32 of the engagement portion 30. The free end surface 32 is substantially circular. In addition, the engagement protrusions 31 each have a bevelled front end surface 31a. The length of the bevelled front end surface 31a of the engagement projections 31 corresponds substantially to the length of the conical surface of the second recess 9 of the drive portion 6 of the screw element 1, between the free end 5 and the intermediate portion 11. The bevelled front end surface 31a may have the same angle of inclination as the conical recess 9 or the slanted wall 11a of the intermediate portion 11. Such an enlarged bevelled surface facilitates easier location of the drive portion 6 of the screw element 1 even in instances where there is limited visibility or no visibility at the operation site.

Figure 8:
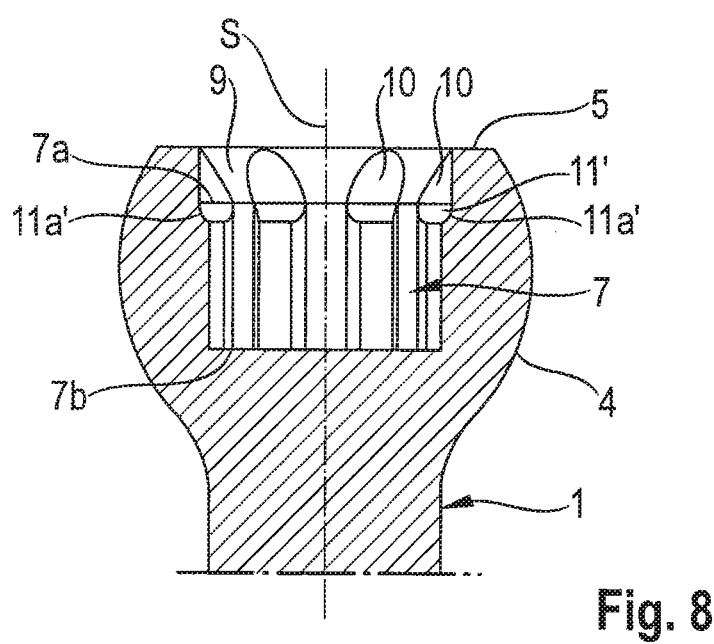
FIG. 8 shows a cross-sectional view of a screw element according to a modified embodiment of the present invention.

A modified embodiment of the screw element with a modified drive portion 6 is shown in FIG. 8. All parts and portions that are identical to the first embodiment are marked with the same reference numerals and the descriptions thereof will not be repeated. The modified embodiment of the screw element differs in the shape of the intermediate portion. In this embodiment, the intermediate portion 11' is formed by a rounded wall 11a'.

Figure 9:
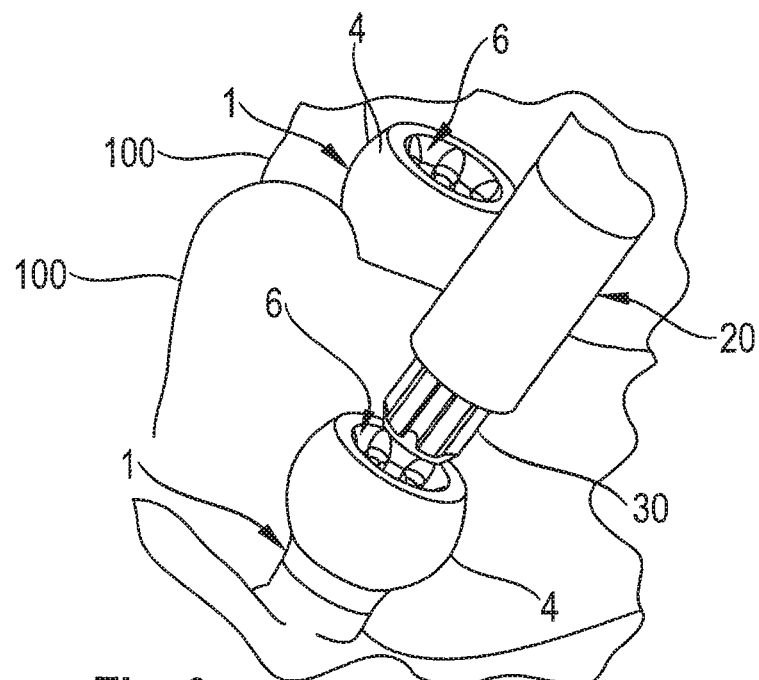
FIG. 9 shows an enlarged perspective view of a step of using the screw element and the screw driver according to the first embodiment.
Figure 10:
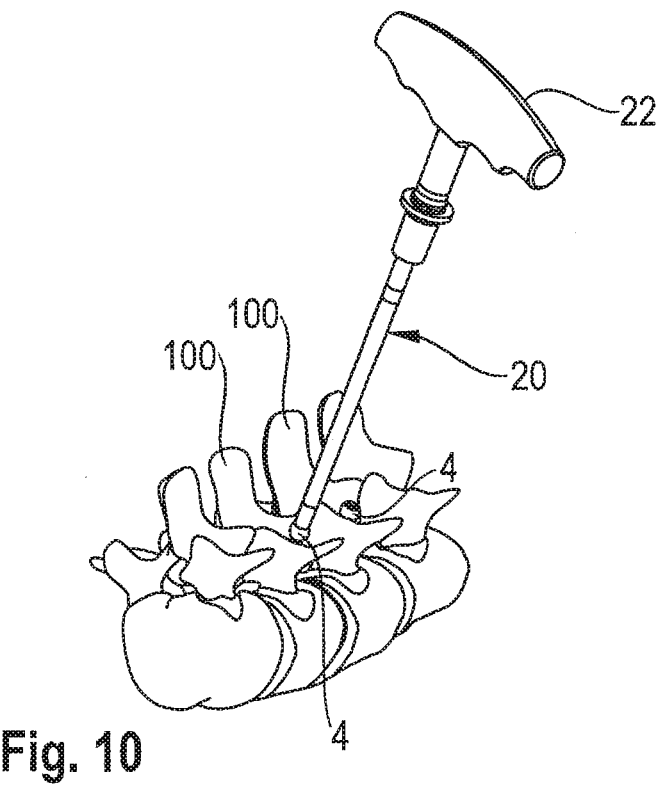
FIG. 10 shows a perspective view of a step of adjusting an insertion depth of the screw element according to the first embodiment.

Referring now to FIGS. 9 and 10, the application of the screw element and the screw driver according to the first embodiment will be explained. In FIG. 9, two screw elements 1 have already been inserted into the pedicles of two vertebrae 100. Each of the screw elements 1 includes the drive portion 6 as described above. The insertion depths of the screw elements 1 are further adjusted with the screw driver 20 by engaging the engagement portion 30 with the corresponding drive portions 6 of the screw elements 1. Due to the design of the drive portion 6 of the screw element 1 and the engagement portion 30 of the screw driver 20, the engagement portion 30 and the drive portion 6 can be quickly and easily engaged, even if there is limited or no visibility at the operation site. Therefore, it is possible to adjust multiple pedicle screws in a short time.

Figure 11A:
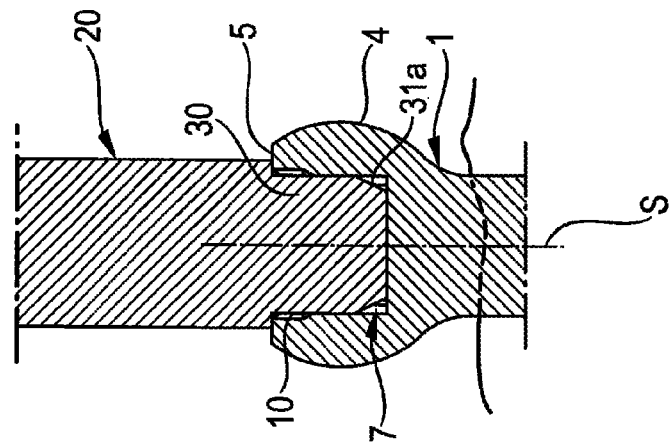
FIGS. 11a-11c show cross-sectional views of steps of engaging the drive portion of the screw element with the engagement portion of the screw driver according to the first embodiment.
Figure 11B:
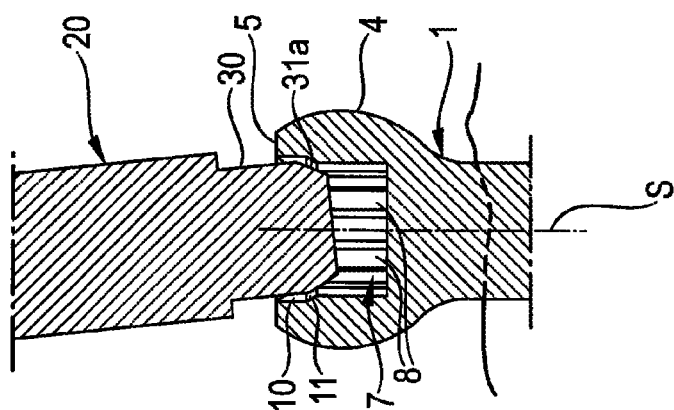
Figure 11C:
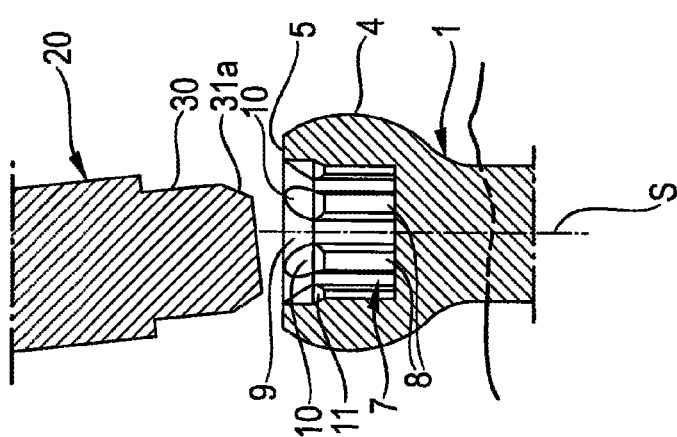

Referring now to FIGS. 11a, 11b, and 11c, the interaction between the engagement portion 30 of the screw driver 20 and the drive portion 6 of the screw element 1 is shown in more detail. As depicted in FIG. 11a, the screw driver 20 may approach the screw element 1 at an incline relative to the screw axis S. As further shown in FIGS. 11a and 11b, the engagement portion 30 of the screw driver 20 may first engage the conical second recess 9. When the engagement protrusions 31 of the engagement portion 30 of the screw driver 20 begin to engage the guide grooves 10, the screw driver 20 is automatically aligned with the screw element 1 while penetrating or advancing further into the drive portion 6. The guide grooves 10 and the intermediate portion 11 guide the engagement portion 30 into the drive grooves 8, so that the screw element 1 and the screw driver 20 become aligned and connected in a form-fit manner to each other. Then, torque can be applied with the screw driver 20 onto the screw element 1. Due to the decreasing depth and width of the guide grooves 10 towards the free end 5 and the bottom lines $B_g$, respectively, the engagement portion 30 can be easily rotated until the engagement protrusions 31 locate and engage the engagement grooves 10.

Figure 12:
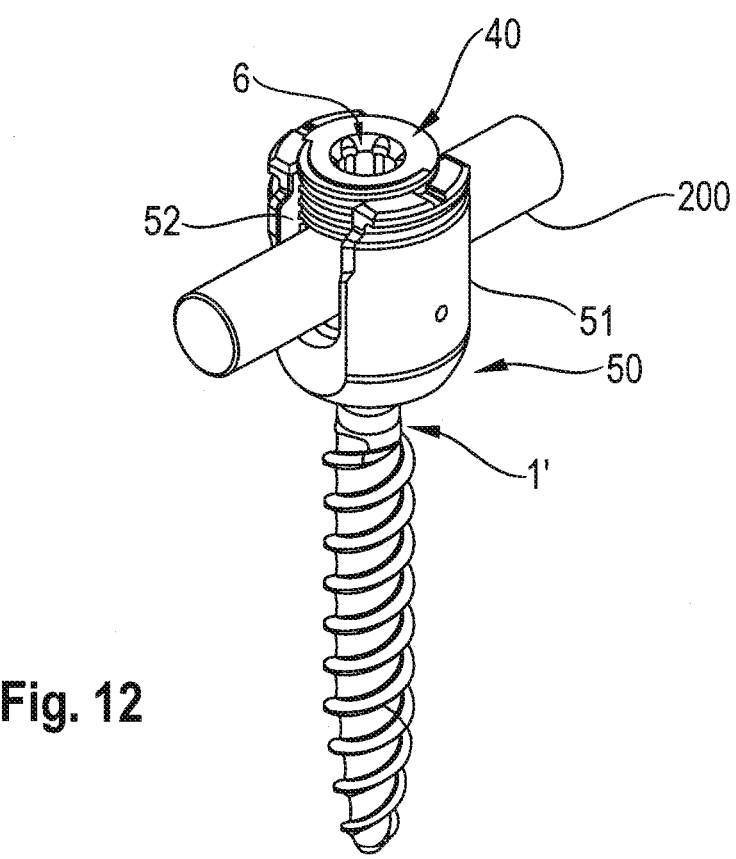
FIG. 12 shows a perspective view of a second embodiment of the screw element as part of a polyaxial bone anchor.

A second embodiment of a screw element is explained with reference to FIG. 12. Parts and portions that are the same or substantially the same as the previous embodiments have the same reference numerals and the descriptions thereof will not be repeated. In the embodiment of FIG. 12, the screw element is a set screw 40 that is used in a polyaxial bone anchoring device 50. The polyaxial bone anchoring device 50 is shown only in an exemplary manner; many different designs of such polyaxial bone anchoring device may be contemplated. The polyaxial bone anchoring device 50 includes a screw element 1' that has a spherical segment-shaped head (not shown) and a drive portion. The drive portion may be a known drive portion, such as, for example, a known torx-shaped drive portion or a polygon-shaped drive portion, or may be a drive portion 6 according to the previously described embodiments. The screw element 1' is pivotably connected to a receiving part 51 that includes a seat to hold the head of the screw element 1' in a ball and socket manner. A pressure element (not shown) may also be provided to exert pressure onto the head. The receiving part 51 also includes a substantially U-shaped recess 52 that is configured to receive a rod 200 therein. The rod 200 may be connected to a plurality of bone anchoring devices. To lock the rod 200 in the receiving part 51 and a pivot position of the head relative to the receiving part 51, a locking element in the form of a set screw 40 is used that cooperates with a thread provided in the receiving part 51. Once the head and the rod are locked, further adjustments may become necessary. To make such adjustments, the set screw 40 has to be loosened and tightened again after correcting the angular position of the receiving part 51 relative to the head or after correcting the position of the rod 200. For such adjustments, the screw driver 20 that cooperates with the drive portion 6 in the set screw 40 may be used. Hence, the adjustments can be performed more quickly and easily.

It should be noted that a set screw having the engagement portion 6 could also be used for other types of bone anchoring devices, for example, for a monoaxial bone anchor in which the screw element and the receiving part are fixed relative to each other.

Figure 13:
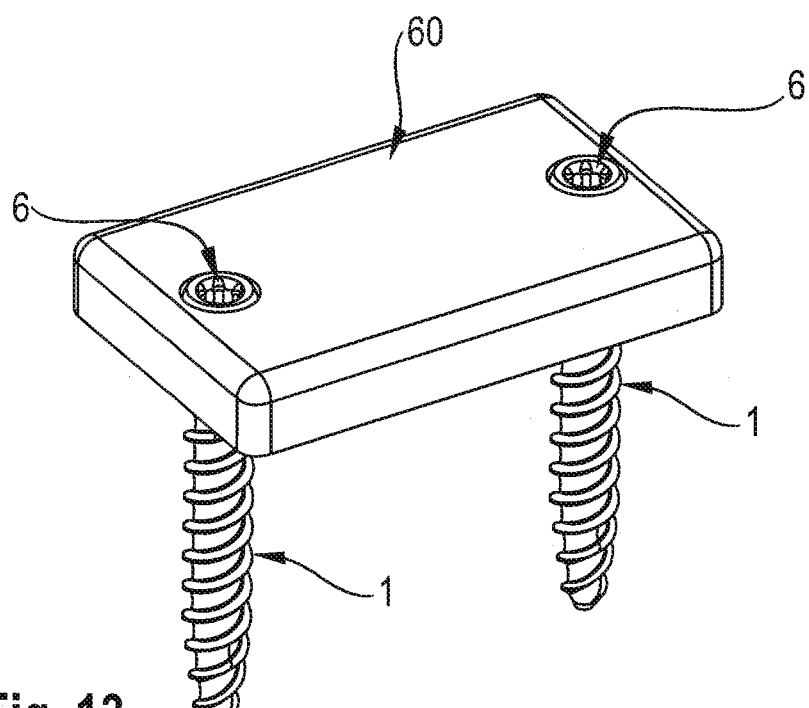
FIG. 13 shows a perspective view of a further application of the screw element in connection with a bone plate.

A further application is shown in FIG. 13. FIG. 13 depicts a bone plate 60 that may be used with the screw elements 1, for example, in orthopedic and trauma surgery to immobilize broken bone parts. The screw elements 1 can be the same or similar to those discussed with respect to FIGS. 1 to 5 and 8, where the head of each screw element 1 includes the drive portion 6. The head may have a spherical segment shape so that the screw element 1 can be placed and positioned within a hole of the bone plate 60 at various angles. Alternatively, the head may have a shape that limits positioning of the screw element 1, for example, to a fixed angle with respect to the bone plate 60. When implanting the bone plate 60, the insertion depth of the screw elements 1 may need to be adjusted. These adjustments may be made by using the screw element 1 with the drive portion 6 and a corresponding screw driver 20. In a still further modification, a locking element may be provided in the holes of the bone plate 60 to prevent pull-out of the screw elements, where the drive portion 6 is formed on the locking elements.

Further embodiments and modifications of the previously described embodiments may also be contemplated. For example, the sizes and the angles of the bevelled surface of the second recess 9, of the guide grooves 8, as well as of the intermediate portion 11, 11' can be varied. The wall 11a, 11a' of the intermediate portion 11, 11' may also have any shape that is configured to guide the engagement portion 30 of the screw driver 20 into the first recess 7.

In the embodiments shown, an even number of drive grooves 8 are shown, and each drive groove 8 is positioned opposite to another drive groove 8 in the drive portion 6. However, an odd number of drive grooves may also be contemplated, and one drive groove may not be opposite to another drive groove in the drive portion. This may also apply to the corresponding guide grooves.

In addition, instead of the torx-shape of the drive grooves, a polygonal shape of the first recess may also be contemplated. In such a case, the corners of the polygon may be considered the drive grooves.

In some embodiments, the respective bottom lines of the drive grooves and the guide grooves may not align and instead may be arranged in a twisted configuration around the screw axis. Also, the respective bottom lines may not be exactly parallel to the screw axis in some embodiments.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

The invention claimed is:

1. A screw element for use in spinal, orthopedic, or trauma surgery, the screw element comprising:
   a screw axis;
   a shank extending along the screw axis and configured to be inserted in a bone; and
   a drive portion configured to engage a screw driver, wherein the drive portion comprises:
      a first wall defining a first recess, wherein a plurality of drive grooves are formed in the first wall and extend parallel to the screw axis; and
      a second wall defining a second recess, wherein the second wall extends axially from the first wall to a free end portion of the screw element, and wherein in a first radial direction relative to the screw axis, a distance between the screw axis and the second wall continuously increases from the first wall to the free end portion;
   wherein a plurality of guide grooves are formed in the second wall at circumferential positions around the screw axis that correspond respectively to circumferential positions of the drive grooves, wherein the guide grooves extend further radially from the screw axis than the drive grooves and are configured to guide an engagement portion of the screw driver from the free end portion of the screw element to the drive grooves, and wherein in a second radial direction relative to the screw axis that corresponds to one of the guide grooves, a distance between the screw axis and at least a portion of the second wall remains constant as the second wall extends axially.

2. The screw element of claim 1, wherein the first recess is substantially cylindrical.

3. The screw element of claim 1, wherein the first recess has a torx-shape.

4. The screw element of claim 1, wherein the second recess is substantially conical.

5. The screw element of claim 1, wherein an axial length of the second recess is between one fifth and one half of an axial length of the first recess.

6. The screw element of claim 5, wherein the axial length of the second recess is between one fourth and one third of the axial length of the first recess.

7. The screw element of claim 1, wherein the guide grooves each has a bottom that extends along a first line, wherein the drive groove each has a bottom that extends along a second line, and wherein the first line is located further away from the screw axis than the corresponding second line is from the screw axis.

8. The screw element of claim 1, wherein a depth of the guide grooves increases in a direction from the free end portion of the screw element towards the first recess.

9. The screw element of claim 1, wherein a maximum width of the guide grooves increases in a direction from the free end portion of the screw element towards the first recess.

10. The screw element of claim 1, wherein a width of the guide grooves is greater than a width of the drive grooves at a position closest to the first recess.

11. The screw element of claim 1, wherein each of the guide grooves has an inclined shoulder adjacent to each respective drive groove.

12. The screw element of claim 1, wherein the screw element is a bone screw, at least a portion of the shank comprises a bone thread, wherein the bone screw further comprises a head having the free end portion on a side opposite to the shank, and wherein the drive portion is provided on the head.

13. The screw element of claim 11, wherein the head has a spherical segment-shaped outer surface portion.

14. The screw element of claim 1, wherein the screw element is a set screw configured to be used as a locking element for a polyaxial bone screw or for a bone plate.

15. The screw element of claim 1, wherein respective tapered surfaces connect each of the guide grooves with a corresponding one of the drive grooves in the axial direction, and wherein the first wall connects adjacent tapered surfaces in the circumferential direction.

16. A system comprising:
a screw element for use in spinal, orthopedic, or trauma surgery, the screw element comprising:
a screw axis;
a shank extending along the screw axis and configured to be inserted in a bone; and
a drive portion configured to engage a screw driver, wherein the drive portion comprises a first wall defining a first recess, wherein a plurality of drive grooves are formed in the first wall and extend parallel to the screw axis, and wherein the drive portion further comprises a second wall defining a second recess, wherein the second wall extends axially from the first wall to a free end portion of the screw element, and wherein in a first radial direction relative to the screw axis, a distance between the screw axis and the second wall continuously increases from the first wall to the free end portion;
wherein a plurality of guide grooves are formed in the second wall at circumferential positions around the screw axis that correspond respectively to circumferential positions of the drive grooves, wherein the guide grooves extend further radially from the screw axis than the drive grooves, and wherein in a second radial direction relative to the screw axis that corresponds to one of the guide grooves, a distance between the screw axis and at least a portion of the second wall remains constant as the second wall extends axially, and
a screw driver configured to engage the drive portion of the screw element, the screw driver comprising a drive axis and an engagement portion with engagement protrusions each extending parallel to the drive axis;
wherein the guide grooves of the drive portion are configured to guide the engagement portion of the screw driver from the free end portion of the screw element to the drive grooves, wherein the engagement protrusions are configured to engage the drive grooves, and wherein the engagement protrusions each comprises a bevelled end.

17. The system of claim 16, wherein the engagement protrusions form a torx-shape in a cross-sectional plane perpendicular to the drive axis.

18. The system of claim 14, wherein the bevelled end of the engagement protrusions have an axial length corresponding substantially to an axial length of the guide grooves.

19. The system of claim 16, wherein when the engagement protrusions of the screw driver are engaged with the drive grooves of the screw element, the screw driver is spaced apart from each of the guide grooves in a radial direction.

20. A method of implanting a screw element in a bone, the screw element comprising a screw axis, a shank extending along the screw axis, and a drive portion comprising a first wall defining a first recess and a second wall defining a second recess, wherein a plurality of drive grooves are formed in the first wall and extend parallel to the screw axis, wherein the second wall extends axially from the first wall to a free end portion of the screw element, and wherein in a first radial direction relative to the screw axis, a distance between the screw axis and the second wall continuously increases from the first wall to the free end portion, wherein a plurality of guide grooves are formed in the second wall at circumferential positions around the screw axis that correspond respectively to circumferential positions of the drive grooves, wherein the guide grooves extend further radially from the screw axis than the drive grooves, and wherein in a second radial direction relative to the screw axis that corresponds to one of the guide grooves, a distance between the screw axis and at least a portion of the second wall remains constant as the second wall extends axially, the method comprising:
inserting the shank of the screw element into the bone;
engaging the drive portion of the screw element with a screw driver, wherein the guide grooves are configured to guide an engagement portion of the screw driver from the free end portion of the screw element to the drive grooves; and using the screw driver to adjust a position of the screw element relative to the bone when the engagement portion of the screw driver is engaged with the drive grooves of the screw element.

21. The method of claim 20, wherein the screw driver has a drive axis, and wherein when the engagement portion of the screw driver engages the second recess of the screw element while the screw axis and the drive axis are not aligned, the guide grooves are configured to facilitate alignment of the drive axis with the screw axis and engagement of the engagement portion of the screw driver with the drive grooves of the screw element.

22. The method of claim 20, wherein the engagement portion of the screw driver comprises engagement protrusions, and wherein the guide grooves are configured to guide each of the engagement protrusions into a respective one of the drive grooves.

23. A screw element for use in spinal, orthopedic, or trauma surgery, the screw element comprising:
   a screw axis;
   a shank extending along the screw axis and configured to be inserted in a bone; and
   a drive portion configured to engage a screw driver, wherein the drive portion comprises:
      a first wall having a cylinder segment-shaped portion defining a first recess extending along the screw axis,
      wherein a plurality of drive grooves are formed in the cylinder segment-shaped portion of the first wall and extend parallel to the screw axis; and
   a second wall defining a second recess, wherein the second wall extends axially from a free end portion of the screw element to the first wall, and wherein along a first direction perpendicular to the screw axis, the second wall has an inner width that is greater than an inner width of the first wall along the first direction;
wherein a plurality of guide grooves are formed in the second wall at circumferential positions around the screw axis that correspond respectively to circumferential positions of the drive grooves, wherein the guide grooves extend further radially from the screw axis than the drive grooves, and wherein respective inclined portions directly connect a corresponding guide groove with a corresponding drive groove in an axial direction to guide an engagement portion of the screw driver from the free end portion of the screw element to the drive grooves,
wherein at least part of each of the inclined portions is at a same axial height as part of the cylinder segment-shaped portion of the first wall, such that a cross-section taken along at least one plane perpendicular to the screw axis passes through the inclined portions and the cylinder segment-shaped portion of the first wall.

* * * * *

UNITED STATES PATENT AND TRADEMARK OFFICE
CERTIFICATE OF CORRECTION

PATENT NO.         : 9,867,639 B2
APPLICATION NO.    : 14/685433
DATED              : January 16, 2018
INVENTOR(S)        : Lutz Biedermann et al.

Page 1 of 1

It is certified that error appears in the above-identified patent and that said Letters Patent is hereby corrected as shown below:

In the Claims

Column 7, Line 49, Claim 13, delete "claim 11" and insert -- claim 12 --

Column 8, Line 36, Claim 18, delete "claim 14" and insert -- claim 16 --

Signed and Sealed this
Eleventh Day of December, 2018

Andrei Iancu
*Director of the United States Patent and Trademark Office*